United States Patent
Birkhold et al.

(10) Patent No.: US 12,296,191 B2
(45) Date of Patent: May 13, 2025

(54) DOSE ESTIMATION FOR THE IRRADIATION OF AN OBJECT

(71) Applicant: Siemens Healthcare GmbH, Erlangen (DE)

(72) Inventors: Annette Birkhold, Nuremberg (DE); Philipp Roser, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 847 days.

(21) Appl. No.: 17/246,866

(22) Filed: May 3, 2021

(65) Prior Publication Data

US 2021/0353961 A1 Nov. 18, 2021

(30) Foreign Application Priority Data

May 13, 2020 (DE) ...................... 10 2020 205 996.9

(51) Int. Cl.
  *A61N 5/10* (2006.01)
  *G06T 3/4007* (2024.01)
  (Continued)

(52) U.S. Cl.
  CPC .......... *A61N 5/1031* (2013.01); *G06T 3/4007* (2013.01); *G06T 5/10* (2013.01);
  (Continued)

(58) Field of Classification Search
  None
  See application file for complete search history.

(56) References Cited

U.S. PATENT DOCUMENTS

2007/0263227 A1* 11/2007 Mujat ................. G06T 7/149
  356/497
2012/0326057 A1* 12/2012 Remeijer ............. A61N 5/1031
  250/492.1
(Continued)

FOREIGN PATENT DOCUMENTS

DE   102017216671 A1 *  4/2018 ............ G01N 23/04
WO      2019199644 A1    10/2019

OTHER PUBLICATIONS

Adam Glaser, Applications of Cherenkov Light Emission for Dosimetry in Radiation Therapy, May 2015 (Year: 2015).*
(Continued)

*Primary Examiner* — John E Johansen
*Assistant Examiner* — Michael Paul Mirabito
(74) *Attorney, Agent, or Firm* — Lempia Summerfield Katz LLC

(57) ABSTRACT

In accordance with a method for dose estimation for the irradiation of an object, a model with a total number of spatial elements is provided on a memory element. For each spatial element, the model specifies a material composition of the object. A neighborhood material composition is determined for a neighborhood of spatial elements depending on the model by a computing unit. A radiation dose for the neighborhood with regard to an ionizing radiation is determined with aid of a simulation depending on the neighborhood material composition. A dose distribution for the object with regard to the ionizing radiation is determined based on the radiation dose for the neighborhood.

16 Claims, 1 Drawing Sheet

(51) Int. Cl.
G06T 5/10      (2006.01)
G06T 5/70      (2024.01)
G06T 7/149     (2017.01)

(52) U.S. Cl.
CPC ........... *G06T 5/70* (2024.01); *G06T 7/149* (2017.01); *A61N 2005/1034* (2013.01); *A61N 5/1071* (2013.01)

(56) References Cited

U.S. PATENT DOCUMENTS

2013/0030762 A1* 1/2013 Mercier .............. A61N 5/1031 702/179
2021/0016109 A1* 1/2021 Sjölund ............... A61N 5/1031

OTHER PUBLICATIONS

Badal, Andreu, and Aldo Badano. "Accelerating Monte Carlo simulations of photon transport in a voxelized geometry using a massively parallel graphics processing unit." Medical physics 36.11 (2009): 4878-4880.

Bert, Julien, et al. "Geant4-based Monte Carlo simulations on GPU for medical applications." Physics in Medicine & Biology 58.16 (2013): 5593-5611.

He, Kaiming, Jian Sun, and Xiaoou Tang. "Guided image filtering." IEEE transactions on pattern analysis and machine intelligence 35.6 (2013): 1397-1409.

Kawrakow, Iwan. "On the de-noising of Monte Carlo calculated dose distributions." Physics in Medicine & Biology 47.17 (2002): 3087-3103.

Miao, Binhe, et al. "Adaptive anisotropic diffusion filtering of Monte Carlo dose distributions." Physics in Medicine & Biology 48.17 (2003): 2767-2781.

Roser, Philipp, et al. "Physics-driven learning of x-ray skin dose distribution in interventional procedures." Medical physics 46.10 (2019): 4654-4665.

Schegerer, Alexander, et al. "Diagnostic reference levels for diagnostic and interventional X-ray procedures in Germany: update and handling." RöFo-Fortschritte auf dem Gebiet der Röntgenstrahlen und der bildgebenden Verfahren. vol. 191. No. 08. © Georg Thieme Verlag KG, 2019. pp. 739-751.

Schmidt, B., and W. A. Kalender. "A fast voxel-based Monte Carlo method for scanner-and patient-specific dose calculations in computed tomography." Physica Medica-European Journal of Medical Physics 18.2 (2002): 43-53.

Woodcock, E., et al. "Techniques used in the GEM code for Monte Carlo neutronics calculations in reactors and other systems of complex geometry." Proc. Conf. Applications of Computing Methods to Reactor Problems. (1965). pp. 557-579.

Zhong, Xia, et al. "A machine learning pipeline for internal anatomical landmark embedding based on a patient surface model." International journal of computer assisted radiology and surgery 14.1 (2019): 53-61.

Zhong, Xia, et al. "Generation of personalized computational phantoms using only patient metadata." Proc IEEE NSS/MIC. 2017. pp. 1-3.

German Office Action for German Application No. 10 2020 205 996.9 dated Feb. 25, 2021.

* cited by examiner

DOSE ESTIMATION FOR THE IRRADIATION OF AN OBJECT

The present patent document claims the benefit of German Patent Application No. 10 2020 205 996.9, filed May 13, 2020, which is hereby incorporated by reference in its entirety.

TECHNICAL FIELD

The present disclosure relates to a computer-implemented method for dose estimation for the irradiation of an object with an ionizing radiation, to a method for setting parameters for the irradiation of an object, to a method for imaging of an object, to an arrangement for dose estimation, to an irradiation apparatus, and to a computer program product.

BACKGROUND

During the irradiation of objects with ionizing radiation and during the imaging of objects based on ionizing radiation, awareness of the radiation dose, also as a consequence of legal stipulations, which require evidence of a consistent dose application, has increased in recent years. The rapid and precise determination of an object-specific dose distribution, in particular for predicting stochastic and deterministic risk factors and for monitoring the dose, is of relevance.

In existing approaches to x-ray imaging, a Monte-Carlo simulation of the particle transport has been employed for computational dose estimation, for instance.

These methods have a very high algorithmic complexity, however, so that the effort of computing reliable Monte-Carlo simulations is an obstacle to their widespread use.

SUMMARY AND DESCRIPTION

An object of the present disclosure is therefore to specify an improved concept for dose estimation during the irradiation of an object with an ionizing radiation, through which the computational effort and accordingly the time required for the dose estimation is reduced.

The scope of the present disclosure is defined solely by the appended claims and is not affected to any degree by the statements within this summary. The present embodiments may obviate one or more of the drawbacks or limitations in the related art.

The idea behind the improved concept, starting from a spatially discrete modeling of the material composition of the object for a coherent neighborhood of a plurality of spatial elements, is to determine an effective homogenous material composition and, based thereon, to carry out a simulation for the radiation dose. The dose distribution for the object may be determined for individual neighborhoods for the radiation doses determined in this way.

In accordance with the improved concept, a computer-implemented method for dose estimation for the irradiation of an object with an, in particular predefined, ionizing radiation is specified. In this case, a three-dimensional model (e.g., discrete 3D model) with a total number of spatial elements is provided on a memory element. The model specifies a material composition of the object for each spatial element. The three-dimensional model may be based on an earlier recording of the same object. Alternatively, there may be an underlying statistical model, which may have been matched in particular with the object in terms of size and form, or there may be an underlying generic model. A neighborhood material composition is determined for a coherent neighborhood of spatial elements of the total number of spatial elements depending on the model by a computing unit. By the computing unit, a radiation dose for the neighborhood with regard to the ionizing radiation may be determined with the aid of a simulation depending on the neighborhood material composition. By the computing unit, a dose distribution for the object with regard to the ionizing radiation is determined based on the radiation dose for the neighborhood.

The object may involve a human being or any other living thing or a non-living object, for instance. The irradiation of the object may serve, for example, to examine, analyze, modify, or treat the object with the ionizing radiation. The irradiation may serve, for example, for image-based analysis or examination or imaging of the object. For living things, the irradiation may also be used for medical treatment or therapy.

In accordance with the model, the object or a part of the object is described as a discrete approximation by the total number of the spatial elements. In this case, the spatial elements may also be referred to as voxels.

Therefore, in accordance with the model, a material composition is given for each spatial element of the total number of spatial elements. In particular, in accordance with the model, the material composition is homogeneous within each individual spatial element. Different spatial elements, (e.g., different neighboring spatial elements or different spatial elements of the neighborhood), may have material compositions that differ from one another in such cases. In the case of living things, the different material compositions of different spatial elements may be attributed to different types of tissue, for example.

The neighborhood of spatial elements may be understood as a plurality of spatial elements of the total number of spatial elements, wherein the plurality is smaller than the total number. The spatial elements of the neighborhood are coherent, so that any given pair of spatial elements of the neighborhood is either directly adjacent to another or is indirectly connected to another via one or more further spatial elements of the neighborhood. In particular, the coherent neighborhood may be a simple coherent part of the discrete space, given by the total number of spatial elements.

For example, all spatial elements that are located within a predefined three-dimensional geometrical figure, for example a rectangle with defined edge lengths, to which spatial elements of the neighborhood belong. Other definitions of the neighborhood are likewise possible, however.

The neighborhood material composition is in particular homogeneous within the neighborhood. In other words, the material composition is the same for all spatial elements of the neighborhood.

In other words, from the different material compositions of the individual spatial elements of the neighborhood, a fictional or effective neighborhood material composition is constructed, which in respect of its physical properties describes all spatial elements of the neighborhood approximately in the same way. In other words, the determination of the neighborhood material composition for the neighborhood in this way may be regarded as a reduction in the resolution of the model.

The determination of the neighborhood material composition depending on the model includes in particular the determination of the neighborhood material composition depending on the respective material compositions of all spatial elements of the neighborhood. To this end, for example, one or more material parameters of the individual material compositions may be averaged or homogeneously approximated in some other way, so that to a certain extent an effective or fictional material is constructed for the entire neighborhood.

In order to determine the radiation dose for the neighborhood, it is assumed in particular that the predefined ionizing radiation strikes the object or the neighborhood with the neighborhood material composition as described. The radiation dose in this case corresponds for example to a constant value for the neighborhood.

The dose distribution for the object includes a corresponding value for the radiation dose in particular for each spatial element of the total number of spatial elements.

In accordance with the method according to the improved concept, the corresponding value for the radiation dose is determined approximately for all spatial elements of the neighborhood depending on the radiation dose for the entire neighborhood.

The acts described may be carried out in particular for further neighborhoods of the total number of spatial elements, so that for each neighborhood a radiation dose is determined with the aid of the corresponding neighborhood material composition and ultimately the dose distribution is established based on all radiation doses determined for the different neighborhoods.

The ionizing radiation may involve x-ray radiation, $\alpha$ radiation, $\beta$ radiation, or neutron radiation, for example. The ionizing radiation may also involve electromagnetic radiation, in particular with a wavelength of less than 200 nm, (e.g., ultraviolet radiation or $\gamma$ radiation).

The fact that the ionizing radiation involves a predefined ionizing radiation may be understood in such a way that the type, energy, intensity, and/or wavelength of the radiation are predetermined. For example, the direction of the ionizing radiation relative to the object, in particular, relative to the spatial elements of the total number of spatial elements and thus also to the neighborhood and its spatial elements, may be predetermined.

The improved concept, through the effective reduction of the resolution, enables a significant reduction of the computing effort and of the time required for determining the dose distribution, in particular, in high-resolution voxel models, to be made possible without significant disadvantages in respect of the accuracy. The method according to the improved concept may also serve to reduce variants.

Before the simulation is carried out, the effective resolution is reduced by determination of the neighborhood material composition and the simulation is carried out based on the neighborhood. This means that the number of units to be simulated is fewer and a stable solution may still be achieved with little uncertainty. Tests have shown in particular that, with a number of 16 spatial elements per neighborhood, a reduction in precision compared to a full Monte-Carlo simulation of only around 10% is to be expected.

In accordance with at least one form of embodiment of the computer-implemented method according to the improved concept, for a plurality, (i.e., two or more), further coherent neighborhoods of spatial elements of the total number of spatial elements in each case, depending on the model, a respective neighborhood material composition is determined by the computing unit. For each of the further neighborhoods, a further radiation dose with regard to the ionizing radiation is determined with the aid of a simulation depending on the neighborhood material composition of the respective further neighborhood by the computing unit. By the computing unit, the dose distribution for the object based on the further radiation doses is determined for the further neighborhoods and in particular based on all further radiation doses of all further neighborhoods and based on the radiation dose of the neighborhood.

This enables the entire object or an entire region of interest of the object to be taken into consideration, so that a meaningful distribution of the radiation doses is obtained in the form of the dose distribution.

In accordance with at least one form of embodiment, a fluence for the neighborhood with regard to the ionizing radiation is determined by the computing unit depending on the radiation dose. The dose distribution for the object is determined by the computing unit depending on the fluence.

The fluence in this case may be understood as the number of incident photons or other particles of the ionizing radiation on a surface per surface. The fluence is therefore closely interrelated with the irradiation, which specifies the incident radiation energy per surface.

The fluence may be assumed to be approximately proportional to the radiation dose. This is in particular a good approximation if, in the case of large homogeneous spatial elements, a charged particle equilibrium (CPE) may be assumed. In this approximation, the radiation dose may namely be equated with the corresponding collision kerma. In other words, the radiation kerma may be ignored.

The collision kerma in its turn is directly proportional to the fluence, wherein the proportionality factor is given in particular by the corresponding mass attenuation coefficient. The mass attenuation coefficient in this case is equal to the quotients of coefficient of absorption and the density of the corresponding material. In summary, the fluence may thus be determined in accordance with the following relationship:

$$\psi\_N \approx D\_N/(\mu/\rho)\_N,$$

wherein $\psi\_N$ refers to the fluence of the neighborhood N, $D\_N$ to the radiation dose of the neighborhood N, and $(\mu/\rho)\_N$ to the mass attenuation coefficient of the neighborhood N.

In accordance with at least one form of embodiment, a corresponding further fluence for the corresponding further neighborhood with regard to the ionizing radiation is determined by the computing unit depending on each of the further radiation doses. The dose distribution for the object is determined by the computing unit depending on the fluence and the further fluences.

In accordance with at least one form of embodiment, a smoothing filter algorithm is executed by the computing unit depending on the radiation dose for the neighborhood and depending on the further radiation doses for the further neighborhoods, in order to determine the dose distribution for the object.

The smoothing filter algorithm in this case involves an edge-preserving smoothing filter algorithm.

The smoothing filter algorithm enables rapid changes in the dose distribution between different spatial elements or neighborhoods resulting from the effective reduction in resolution to be reduced.

The smoothing filter algorithm is determined in this case depending on the fluence and the further fluences.

A result of the smoothing filter algorithm may therefore be understood as a fluence distribution over spatial elements. The fluence distribution is then again approximately proportional to the dose distribution for the object.

In particular, the dose distribution may be approximately determined in accordance with the relationships:

$$D \approx (\mu/\rho)*\psi, \text{ with } \psi = F(\{\psi\_N\}).$$

Here, relationships D and $\psi$ refer to the dose distribution or the fluence distribution for the object, F to the smoothing filter algorithm, and $\{\psi\_N\}$ to the totality of all fluences for all neighborhoods of spatial elements considered.

In accordance with at least one form of embodiment, the smoothing filter algorithm contains a guided filter algorithm, a Perona-Malik filter algorithm, a Savitzky-Golay filter algorithm, or a bilateral filter algorithm. The Perona-Malik filter algorithm may also be referred to as a Perona-Malik diffusion algorithm or anisotropic diffusion algorithm. The bilateral filter algorithm may also be referred to as a joint bilateral filter algorithm.

These algorithms are especially suitable because of their edge-preserving properties.

Especially advantageous in particular is the guided filter algorithm, in which the mass attenuation coefficient may be used as a guide variable, so that:

$$\psi = GF((\mu/\rho), I(\{\psi\_N\}), r),$$

wherein GF refers to the guided filter algorithm, r to the filter radius, and $(\mu/\rho)$ serves as a guide variable. I refers to a function, (for example, an interpolation function), or the result of an interpolation algorithm.

In accordance with at least one form of embodiment, an interpolation algorithm is executed by the computing unit depending on the radiation dose and on the further radiation doses. The smoothing filter algorithm is executed based on a result of the interpolation algorithm.

The interpolation algorithm in this case may be understood in such a way that for each neighborhood or further neighborhood the result of the interpolation algorithm assigns an associated value for the fluence or the radiation dose to each spatial element within the corresponding neighborhood. In other words, a fluence or radiation dose is first determined for the entire neighborhood and based on the fluence or radiation dose determined in this way, an individual fluence or radiation dose is determined for each spatial element in the neighborhood. In this operation, in one case, the individual fluence or radiation dose may be the same for all spatial elements within the neighborhood. Thus, through the interpolation, the resolution of the voxel model is formally increased again to the original resolution.

In accordance with at least one form of embodiment, the simulation for determining the radiation dose and/or the simulations for determining the further radiation doses include a Monte-Carlo simulation or a finite difference simulation.

In particular, the corresponding Boltzmann equations may be numerically approximately solved by the Monte-Carlo simulation or the finite difference simulation. These simulation methods have proved to be especially robust and precise.

In accordance with the improved concept, a method for setting parameters for the irradiation of an object is also specified. To this end, a predefined first parameter set is defined for the ionizing radiation. Based on the first parameter set, a method for dose estimation in accordance with the improved concept is carried out, in order to define a corresponding dose distribution based on the first parameter set. Depending on the dose distribution determined based on the first parameter set with the aid of the method for dose estimation according to the improved concept, a second parameter set is determined (e.g., automatically) for the ionizing radiation, by the computing unit, for example.

In this case, a parameter set for the ionizing radiation may contain one or more parameters for the radiation or for the application of the radiation within the framework of the irradiation. The parameter sets may contain corresponding values or chronological sequences of values for the energy, wavelength, and/or intensity of the radiation. The parameter sets may also include durations for the irradiation.

In accordance with at least one form of embodiment of the method for setting parameters, the dose distribution determined based on the first parameter set is compared by the computing unit with a target distribution for the dose distribution, a maximum value, or another target value for the dose distribution. The second parameter set is then determined depending on result of the comparison.

In accordance with at least one form of embodiment, a radiation source for generating the ionizing radiation for the irradiation of the object is (e.g., automatically) set depending on the second parameter set.

In accordance with the improved concept, a method for imaging an object is specified. In this case, a method is carried out for setting parameters for the irradiation of the object according to the improved concept. The object is irradiated with ionizing radiation in accordance with the second parameter set, in order to image the object.

The method for imaging of the object in particular involves a non-therapeutic method.

In accordance with the improved concept, an arrangement for dose estimation for the irradiation of an object with an ionizing radiation is also specified. The arrangement has a memory element, which stores a three-dimensional model (e.g., a discrete 3D model) with a total number of spatial elements, wherein the model specifies a material composition of the object for each spatial element of the total number. The arrangement also has a computing unit, which is configured to determine a neighborhood material composition for a coherent neighborhood of spatial elements of the total number of spatial elements depending on the model. The computing unit is configured to determine a radiation dose for the neighborhood with regard to the ionizing radiation with the aid of a simulation depending on the neighborhood material composition and to determine a dose distribution for the object with regard to the ionizing radiation based on the radiation dose for the neighborhood.

Further forms of embodiment of the arrangement for dose estimation in accordance with the improved concept emerge directly from the different forms of embodiment of the computer-implemented method for dose estimation according to the improved concept and vice versa. In particular, an arrangement according to the improved concept may be configured or programmed to carry out a computer-implemented method for dose estimation according to the improved concept or the arrangement carries out such a method.

In accordance with the improved concept, an irradiation apparatus for irradiation of an object is also specified, wherein the irradiation apparatus has an arrangement for dose estimation in accordance with the improved concept. The irradiation apparatus also contains a control unit, which is configured to define a parameter set for an ionizing radiation for irradiation of the object depending on the dose distribution for the object.

In accordance with at least one form of embodiment of the irradiation apparatus, the irradiation apparatus has a radiation source, and the control unit is configured to control the radiation source to emit the ionizing radiation in accordance with the defined parameter set.

In accordance with at least one form of embodiment, the radiation source is embodied as an x-ray radiation source.

Further forms of embodiment of the irradiation apparatus according to the improved concept emerge directly from the different forms of embodiment of the computer-implemented method for dose estimation according to the improved concept, of the method for setting parameters in accordance with the improved concept and of the method for imaging of the object according to the improved concept and vice versa in each case. In particular, the irradiation apparatus according to the improved concept may be configured or programmed to carry out a method according to the improved concept or it carries out such a method.

In accordance with the improved concept, a first computer program is also specified, which includes first commands. When the first commands are executed by a computer system, in particular by an arrangement for dose estimation according to the improved concept, for example, by the computing unit of the arrangement, the first commands cause the computer system to carry out a computer-implemented method for dose estimation according to the improved concept or a method for setting parameters according to the improved concept.

In accordance with the improved concept, a second computer program with second commands is also specified. When the second commands are executed by an irradiation apparatus according to the improved concept, in particular by the computing unit of the irradiation apparatus, the second commands cause the irradiation apparatus to carry out a computer-implemented method for dose estimation according to the improved concept or a method for setting parameters according to the improved concept or a method for imaging of an object according to the improved concept.

In accordance with the improved concept, a computer-readable storage medium is also specified. The computer-readable storage medium stores a first and/or a second computer program according to the improved concept.

The computer programs and also the computer-readable storage medium according to the improved concept may each be understood as computer program products having the first or the second commands.

BRIEF DESCRIPTION OF THE DRAWINGS

The features and combinations of features described here in the description and also below in the description of the figures and/or features and combinations of features described in the figures alone are able to be used not only in the respective combination specified but also in other combinations, without departing from the framework of the disclosure. Embodiments and combinations of features are also to be seen as disclosed that do not have all features of an originally formulated independent claim and/or which go beyond combinations of features set out in the references of the claims or deviate from them.

DETAILED DESCRIPTION

Figure 1:
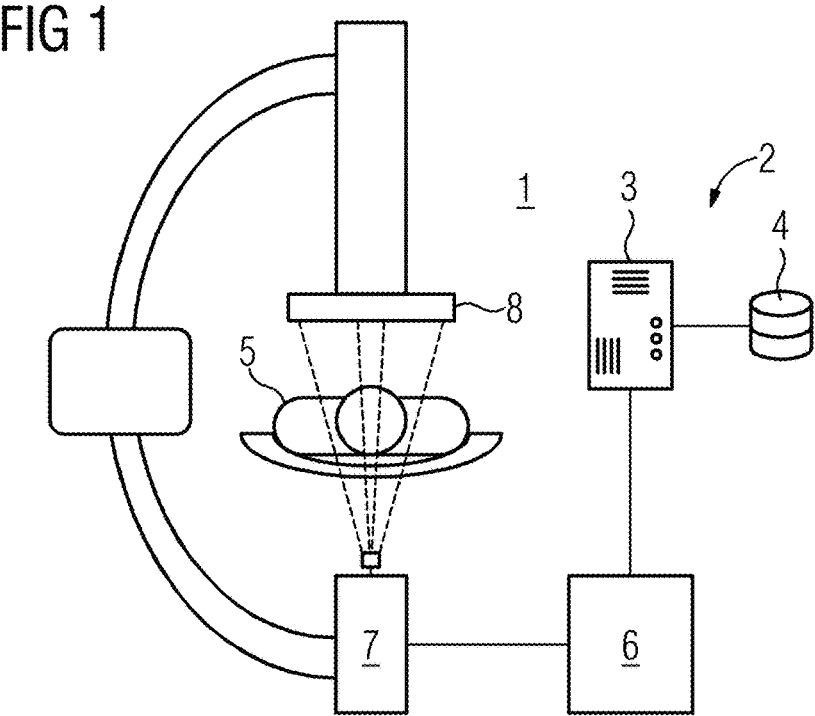
FIG. 1 depicts a schematic block diagram of an example of a form of embodiment of an irradiation apparatus in accordance with the improved concept.

Shown in FIG. 1 is a block diagram of an example of a form of embodiment of an irradiation apparatus 1 for irradiation of an object 5.

The irradiation apparatus 1 has an example of a form of embodiment of an arrangement 2 for dose estimation for the irradiation of the object 5 with ionizing radiation. The arrangement 2 for dose estimation includes a computing unit 3 and a memory element 4, which is coupled to the computing unit 3 or is included in the computing unit.

The irradiation apparatus 1 moreover has a control unit 6 and also a radiation source 7, for example, an x-ray radiation source. The irradiation apparatus 1 may also have a detector 8 for detecting ionizing radiation generated by the radiation source 7 and that has passed at least partly through the object 5. Purely by way of example and in a non-restrictive way, the irradiation apparatus 1 is shown in FIG. 1 as a C-arm device. Depending on the concrete form of embodiment of the irradiation apparatus 1 and depending on the type of radiation used, the irradiation apparatus 1 may also have a different structure.

The control unit 6 is coupled to the radiation source 7 in order to control the latter. The control unit 6 is also coupled to the computing unit 3. The detector 8 may be coupled to the computing unit 3 and/or the control unit 6.

Stored in the memory element 4 is a discrete three-dimensional model, (e.g., a voxel model), which approximately describes the object 5 or a part of the object 5. The basis for the three-dimensional model may be an earlier recording of the same object, for example, or the basis may be a statistical model, which may have been reconciled with the object in size and form, or the basis may be a generic model.

The way in which an irradiation apparatus 1 functions, as is shown in FIG. 1, is explained in more detail below in relation to FIG. 2 with the aid of examples of forms of embodiment of methods according to the improved concept.

Figure 2:
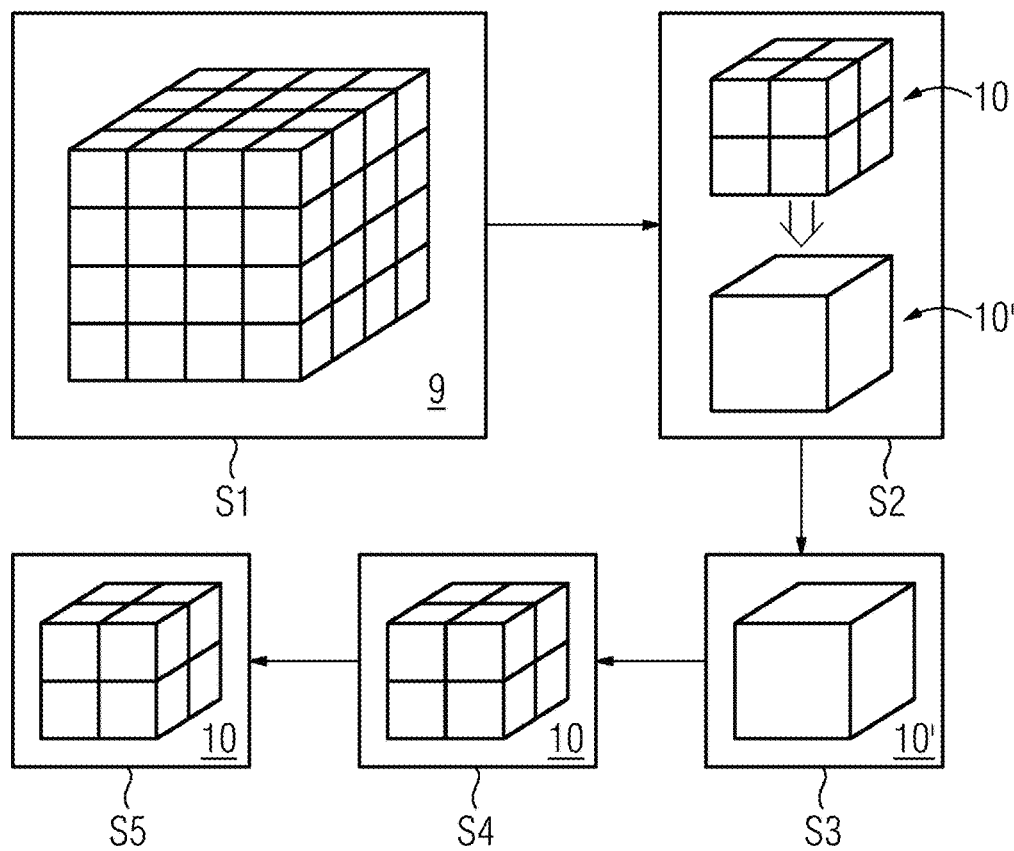
FIG. 2 depicts a flow diagram of an example of a form of embodiment of a computer-implemented method for dose estimation according to the improved concept.

Shown in FIG. 2 is a flow diagram of an example of a form of embodiment of a computer-implemented method for dose estimation according to the improved concept.

In act S1, the model for the object 5 is provided on the memory element 4. The model approximates to the object 5 or a part of the object 5 through a total number 9 of spatial elements or voxels, wherein the memory element 4 stores a material composition of the object 5 for each spatial element of the total number 9 of spatial elements. In this case, the material composition is homogeneous within each spatial element.

In act S2, for a coherent neighborhood 10 of spatial elements based on the model, in particular based on the material compositions of the individual spatial elements, a neighborhood material composition, which is the same for all spatial elements of the neighborhood 10, is determined.

In other words, the neighborhood 10 is treated like an artificially enlarged spatial element 10' with homogeneous effective material composition, namely the neighborhood material composition.

In act S3, a value for a radiation dose of the ionizing radiation is simulated for the neighborhood 10. The simulation may be undertaken based, for example, on a Monte-Carlo simulation or a finite element simulation.

Based on the simulated radiation dose for the neighborhood 10 and, if necessary, based on correspondingly simulated radiation doses for further neighborhoods of the total number 9 of spatial elements, a dose distribution for the object 5 or for the total number 9 of the spatial elements is determined.

In particular, as described in relation to acts S2 and S3, all spatial elements of the total number 9 of spatial elements may be assigned corresponding neighborhoods and corresponding radiation doses may be simulated.

In act S3, for example, for the neighborhood 10 and for all other neighborhoods, a fluence based on the radiation dose simulated in each case is determined. To this end, it may be assumed that an equilibrium of charged particles is present and the radiation dose for a neighborhood 10 is therefore directly proportional to the fluence.

In act S4, for example, for each of the neighborhoods 10, an interpolation, (e.g., a next neighbor interpolation), is carried out, in order formally to restore the original resolution. In particular, each of the spatial elements of a neighborhood 10 is allocated a corresponding fluence depending on the fluence determined for the entire neighborhood 10. In this case, for example, each spatial element within a neighborhood 10 may be assigned the same fluence.

In act S5, a smoothing filter algorithm is applied to all spatial elements or the fluences allocated by the interpolation. In this case, an edge-preserving smoothing filter algorithm is used, in particular, (e.g., a guided algorithm).

As a result of the smoothing filter algorithm, there is now a fluence distribution over all spatial elements of the total number 9 of spatial elements. From the aforementioned approximately directly proportional relationship between fluence and radiation dose, the dose distribution for all spatial elements of the total number 9 of spatial elements may therefore be determined directly from the fluence distribution.

The dose distribution established in this way may be compared with a target distribution or a maximum value for the dose and corresponding parameters for the ionizing radiation may be adapted, (e.g., automatically by the control unit 6 or the computing unit 3), in order to fulfill the target requirements.

Then the control unit 6 may control the radiation source 7, in order to direct the ionizing radiation accordingly onto the object 5, in order to irradiate the object.

As described, in particular, in relation to the figures, it is made possible through the improved concept to determine a reliable estimation of the radiation dose distribution during the irradiation of an object with ionizing radiation with reduced computational effort and reduced variances.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A computer-implemented method for dose estimation for irradiation of an object with an ionizing radiation, wherein a three-dimensional model with a total number of voxels is provided on a memory element, and the three-dimensional model specifies, for each voxel of the total number of voxels, a material composition of the object, the method comprising:
   determining, by a computing unit, a neighborhood material composition in for each coherent neighborhood of a plurality of coherent neighborhoods, depending on the three-dimensional model, wherein each coherent neighborhood comprises a plurality of voxels of the total number of voxels, wherein each neighborhood material composition defines the respective plurality of voxels within the respective coherent neighborhood in a same way, therein resulting in a reduction in a resolution of the three-dimensional model, wherein each coherent neighborhood comprises up to 16 voxels, and wherein a reduction in precision of the three-dimensional model is less than or equal to 10% in comparison to a full Monte-Carlo simulation;
   determining, by the computing unit, a radiation dose for each coherent neighborhood of the plurality of coherent neighborhoods with regard to the ionizing radiation with aid of a simulation depending on the neighborhood material composition of the respective coherent neighborhood of the plurality of coherent neighborhoods;
   determining, by the computing unit, a dose distribution for the object as regards the ionizing radiation based on each radiation dose for each coherent neighborhood of the plurality of coherent neighborhoods, wherein a smoothing filter algorithm is executed by the computing unit in order to determine the dose distribution for the object for the plurality of coherent neighborhoods; and
   irradiating, by a radiation source, the object with the ionizing radiation using the determined dose distribution in order to image the object.

2. The computer-implemented method of claim 1, further comprising:
   determining, depending on the radiation dose, a fluence for each coherent neighborhood of the plurality of coherent neighborhoods with regard to the ionizing radiation; and
   determining the dose distribution for the object depending on the respective fluence for each coherent neighborhood of the plurality of coherent neighborhoods.

3. The computer-implemented method of claim 1, wherein the smoothing filter algorithm comprises a guided filter algorithm, a Perona-Malik filter algorithm, a Savitzky-Golay filter algorithm, or a bilateral filter algorithm.

4. The computer-implemented method of claim 1, wherein an interpolation algorithm is executed by the computing unit depending on the radiation doses, and
   wherein the smoothing filter algorithm is executed based on a result of the interpolation algorithm.

5. The computer-implemented method of claim 1, wherein the simulation for determining the radiation dose comprises a Monte-Carlo simulation or a finite difference simulation.

6. An irradiation apparatus for irradiation of an object, the irradiation apparatus comprising:
   a radiation source;
   a memory configured to store a three-dimensional model with a total number of voxels, wherein, for each voxel of the total number of voxels, the three-dimensional model specifies a material composition of the object;
   a computing unit configured to:
      determine a neighborhood material composition in for each coherent neighborhood of a plurality of coherent neighborhoods, depending on the three-dimensional model, wherein each coherent neighborhood comprises a plurality of voxels of the total number of voxels, wherein each neighborhood material composition defines the respective plurality of voxels within the respective coherent neighborhood in a same way, therein resulting in a reduction in a resolution of the three-dimensional model, wherein each coherent neighborhood comprises up to 16 voxels, and wherein a reduction in precision of the three-dimensional model is less than or equal to 10% in comparison to a full Monte-Carlo simulation;

determine a radiation dose for each coherent neighborhood of the plurality of coherent neighborhoods with regard to ionizing radiation with aid of a simulation depending on the neighborhood material composition of the respective coherent neighborhood of the plurality of coherent neighborhoods; and determine a dose distribution for the object with regard to the ionizing radiation based on each radiation dose for each coherent neighborhood of the plurality of coherent neighborhoods, wherein a smoothing filter algorithm is executed by the computing unit in order to determine the dose distribution for the object for the plurality of coherent neighborhoods; and a control unit configured to:

define a parameter set for an ionizing radiation for irradiation of the object depending on the dose distribution for the object; and control the radiation source to emit the ionizing radiation in accordance with the parameter set defined.

7. The irradiation apparatus of claim 6, wherein the radiation source is an x-ray radiation source.

8. The computer-implemented method of claim 2, wherein the fluence is calculated according to the following relationship:

$$\psi\_N \approx D\_N/(\mu/\rho)\_N,$$

wherein:

$\psi\_N$ refers to the fluence of neighborhood N;

$D\_N$ refers to the radiation dose of the neighborhood N; and $(\mu/\rho)\_N$ refers to a mass attenuation coefficient of the neighborhood N.

9. A computer-implemented method for dose estimation for irradiation of an object with an ionizing radiation, wherein a three-dimensional model with a total number of voxels is provided on a memory element, and the three-dimensional model specifies, for each voxel of the total number of voxels, a material composition of the object, the method comprising:

determining, by a computing unit, a neighborhood material composition in for each coherent neighborhood of a plurality of coherent neighborhoods, depending on the three-dimensional model, wherein each coherent neighborhood comprises a plurality of voxels of the total number of voxels, and wherein each neighborhood material composition defines the respective plurality of voxels within the respective coherent neighborhood in a same way, therein resulting in a reduction in a resolution of the three-dimensional model;

determining, by the computing unit, a radiation dose for each coherent neighborhood of the plurality of coherent neighborhoods with regard to the ionizing radiation with aid of a simulation depending on the neighborhood material composition of the respective coherent neighborhood of the plurality of coherent neighborhoods;

determining, by the computing unit, a dose distribution for the object as regards the ionizing radiation based on each radiation dose for each coherent neighborhood of the plurality of coherent neighborhoods, wherein a smoothing filter algorithm is executed by the computing unit in order to determine the dose distribution for the object for the plurality of coherent neighborhoods; and irradiating, by a radiation source, the object with the ionizing radiation using the determined dose distribution in order to image the object, wherein the dose distribution is calculated according to the following relationship:

$$D \approx (\mu/\rho)^*\psi, \text{ with } \psi=F(\{\psi\_N\}),$$

wherein:

D refers to the dose distribution;

$(\mu/\rho)$ refers to a mass attenuation coefficient;

$\psi$ refers to a fluence distribution for the object;

F refers to the smoothing filter algorithm; and $\{\psi\_N\}$ refers to a totality of all fluences for all neighborhoods of voxels considered.

10. The computer-implemented method of claim 1, wherein the dose distribution is calculated according to the following relationship:

$$D \approx (\mu/\rho)^*\psi, \text{ with } \psi=F(\{\psi\_N\}),$$

wherein:

D refers to the dose distribution;

$(\mu/\rho)$ refers to a mass attenuation coefficient;

$\psi$ refers to a fluence distribution for the object;

F refers to the smoothing filter algorithm; and $\{\psi\_N\}$ refers to a totality of all fluences for all neighborhoods of voxels considered.

11. The irradiation apparatus of claim 6, wherein the computing unit is further configured to:

determine, depending on the radiation dose, a fluence for each coherent neighborhood of the plurality of coherent neighborhoods with regard to the ionizing radiation; and determine the dose distribution for the object depending on the respective fluence for each coherent neighborhood of the plurality of coherent neighborhoods.

12. The irradiation apparatus of claim 11, wherein the fluence is calculated according to the following relationship:

$$\psi\_N \approx D\_N/(\mu/\rho)\_N,$$

wherein:

$\psi\_N$ refers to the fluence of neighborhood N;

$D\_N$ refers to the radiation dose of the neighborhood N; and $(\mu/\rho)\_N$ refers to a mass attenuation coefficient of the neighborhood N.

13. The irradiation apparatus of claim 6, wherein the smoothing filter algorithm comprises a guided filter algorithm, a Perona-Malik filter algorithm, a Savitzky-Golay filter algorithm, or a bilateral filter algorithm.

14. The irradiation apparatus of claim 6, wherein an interpolation algorithm is executed by the computing unit depending on the radiation doses, and wherein the smoothing filter algorithm is executed based on a result of the interpolation algorithm.

15. The irradiation apparatus of claim 6, wherein the simulation for determining the radiation dose comprises a Monte-Carlo simulation or a finite difference simulation.

16. The irradiation apparatus of claim 6, wherein the dose distribution is calculated according to the following relationship:

$$D \approx (\mu/\rho) * \psi, \text{ with } \psi = F(\{\psi\_N\}),$$

wherein:
- D refers to the dose distribution;
- $(\mu/\rho)$ refers to a mass attenuation coefficient;
- $\psi$ refers to a fluence distribution for the object;
- F refers to the smoothing filter algorithm; and
- $\{\psi\_N\}$ refers to a totality of all fluences for all neighborhoods of voxels considered.

* * * * *